United States Patent
Gutmann et al.

(10) Patent No.: US 9,155,768 B2
(45) Date of Patent: Oct. 13, 2015

(54) REGIMEN FOR REDUCING THE APPEARANCE OF THINNING HAIR

(71) Applicants: Erik Edward Gutmann, Minneapolis, MN (US); Anita Marie Grahn, Blaine, MN (US); Nathan Andrew Keen, Anoka, MN (US); Sarah Rosa Peltier, Oakdale, MN (US)

(72) Inventors: Erik Edward Gutmann, Minneapolis, MN (US); Anita Marie Grahn, Blaine, MN (US); Nathan Andrew Keen, Anoka, MN (US); Sarah Rosa Peltier, Oakdale, MN (US)

(73) Assignee: ELC Management LLC, New York, NY (US)

( * ) Notice: Subject to any disclaimer, the term of this patent is extended or adjusted under 35 U.S.C. 154(b) by 128 days.

(21) Appl. No.: 13/627,829

(22) Filed: Sep. 26, 2012

(65) Prior Publication Data

US 2014/0086893 A1    Mar. 27, 2014

(51) Int. Cl.
| | |
|---|---|
| *A61K 36/258* | (2006.01) |
| *A61K 36/28* | (2006.01) |
| *A61K 36/67* | (2006.01) |
| *A61K 36/82* | (2006.01) |
| *A61K 36/9066* | (2006.01) |
| *A61K 36/185* | (2006.01) |
| *A61K 31/60* | (2006.01) |
| *A61K 45/06* | (2006.01) |
| *A61K 31/522* | (2006.01) |
| *A61K 31/7016* | (2006.01) |
| *A61K 36/47* | (2006.01) |
| *A61K 8/368* | (2006.01) |
| *A61Q 5/00* | (2006.01) |
| *A61Q 5/02* | (2006.01) |
| *A61Q 5/12* | (2006.01) |
| *A61K 8/97* | (2006.01) |

(52) U.S. Cl.
CPC ............... *A61K 36/258* (2013.01); *A61K 8/368* (2013.01); *A61K 8/97* (2013.01); *A61K 31/522* (2013.01); *A61K 31/60* (2013.01); *A61K 31/7016* (2013.01); *A61K 36/28* (2013.01); *A61K 36/47* (2013.01); *A61K 45/06* (2013.01); *A61Q 5/002* (2013.01); *A61Q 5/02* (2013.01); *A61Q 5/12* (2013.01); *A61K 2800/28* (2013.01); *A61K 2800/92* (2013.01)

(58) Field of Classification Search
None
See application file for complete search history.

(56) References Cited

U.S. PATENT DOCUMENTS

| | | | |
|---|---|---|---|
| 2002/0035070 A1* | 3/2002 | Gardlik et al. | 514/23 |
| 2004/0105908 A1* | 6/2004 | Suzuki et al. | 424/776 |
| 2005/0084465 A1 | 4/2005 | Baxter | |
| 2010/0047202 A1 | 2/2010 | Goddinger et al. | |
| 2011/0002866 A1* | 1/2011 | Lubit et al. | 424/70.7 |
| 2011/0003016 A1 | 1/2011 | Burry et al. | |

FOREIGN PATENT DOCUMENTS

| | | |
|---|---|---|
| CN | 101415394 | 4/2009 |
| CN | 102008426 | 4/2011 |
| EP | 1685826 | 8/2006 |
| FR | 2884828 | * 10/2006 |
| JP | 07-017833 | 1/1995 |
| JP | 11-092337 | 4/1999 |
| JP | 11-092338 | 4/1999 |
| JP | 2004-018526 | 1/2004 |
| JP | 2007-023038 | 2/2007 |
| JP | 2007-302575 | 11/2007 |
| KR | 10-2006-0046961 | 5/2006 |
| KR | 101029973 | 4/2011 |
| WO | WO-0230367 | 4/2002 |
| WO | WO-2007/112433 | 10/2007 |
| WO | WO-2009/053431 | 4/2009 |

OTHER PUBLICATIONS

Website document entitled "Keranique Products for Hair Loss". Sep. 8, 2011. 5-pages, Obtained from http://www.hairlosshell.com/keranique-products-for-hair-loss.*
Website document entitled "Ookisa Hair Care—Shampoo, Conditioner, Soufflé and Serum review". May 31, 2011. 8-pages. Obtained from http://weheartthis.com.*
PCT International Search Report; International Application No. PCT/US2012/058024; Completion Date: Mar. 22, 2013; Mailing Date: Mar. 25, 2013.
PCT Written Opinion of the international Searching Authority; International Application No. PCT/US2012/058024; Completion Dale: Mar. 22, 2013; Mailing Date: Mar. 25, 2013.
Supplemental European Search Report; EP12837467.5; Mailing Date: Jun. 8, 2015; Completion Date: May 27, 2015.

* cited by examiner

*Primary Examiner* — Chris R Tate
(74) *Attorney, Agent, or Firm* — Idris McKelvey

(57) ABSTRACT

A method for reducing the appearance of thinning hair comprising the successive steps of: a) treating hair with an exfoliating shampoo composition comprising at least one chemical exfoliant; b) treating hair with a conditioner comprising at least one natural conditioning polymer and at least one natural stimulant; c) treating hair with a scalp serum comprising at least one natural extract, and salicylic acid.

7 Claims, No Drawings

REGIMEN FOR REDUCING THE APPEARANCE OF THINNING HAIR

CROSS-REFERENCE TO RELATED APPLICATIONS

This application claims priority from U.S. Provisional Application No. 61/541,774 filed Sep. 30, 2011.

FIELD OF THE INVENTION

The present invention relates to a method for reducing the appearance of thinning hair via a regimen of naturally-based personal care treatment products. In one embodiment, the personal care products are enhanced by an oral herbal supplement.

BACKGROUND OF THE INVENTION

Thinning hair is generally linked to underlying scalp conditions. Such scalp conditions are generally treated with standard topical compositions, most often lotions, creams, pastes, gels, ointments, salves and milks, delivery forms developed and optimized for use in treating bare skin. These vehicles are generally unsuitable for application to hair, as a large proportion of the composition sticks to the hair and do not contact the scalp.

Pharmaceutical compositions specifically formulated for delivering active pharmaceutical ingredients to the scalp are generally of one of three delivery forms: shampoos, conditioners and serums.

A shampoo or conditioner pharmaceutical composition for the delivery of an active pharmaceutical ingredient to the scalp is often used. An amount of solution is poured on the head and quickly rubbed into the scalp with the fingers. But it is generally difficult to apply a correct dose of an active pharmaceutical ingredient using a solution. A solution often drips away from the scalp, frequently into the eyes.

A serum, generally in spray form, may be effective for the delivery of an active pharmaceutical ingredient to the scalp and overcomes many of the problems associated with a shampoo or conditioner composition. The amount of composition applied to the hair is more easily regulated, making proper dosing relatively simple. There is reduced run-off and dripping when compared to a shampoos and conditioners.

One drawback of spray-type serums is that if they are applied to hair which suffers from oily build-up or has been previously treated with heavy shampoos or conditioners, the actives may be impeded from providing sufficient efficacy to the scalp. Therefore, there is a need for a personal care regimen which "primes" the scalp for treatment from a serum. Furthermore, there is a need for a regimen which employs largely naturally based ingredients in order to avoid build-up associated with repeated use of synthetic shampoo compositions.

SUMMARY OF THE INVENTION

The present invention relates to a method for reducing the appearance of thinning hair comprising the successive steps of: a) treating hair with an exfoliating shampoo composition comprising at least one chemical exfoliant; b) treating hair with a conditioner comprising at least one natural conditioning polymer and at least one natural stimulant; c) treating hair with a scalp serum comprising at least one vitamin, at least one natural extract, and salicylic acid.

The method may further include the step of ingesting a capsule, the contents of the capsule comprising gotu kola, turmeric root, green tea leaf, triphala powder, black pepper extract, and glycerin.

DETAILED DESCRIPTION OF THE INVENTION

While the specification concludes with claims that particularly point out and distinctly claim the invention, it is believed the present invention will be better understood from the following description.

All percentages, parts and ratios are based upon the total weight of the compositions of the present invention, unless otherwise specified. All such weights as they pertain to listed ingredients are based on the active level, and, therefore, do not include solvents or by-products that may be included in commercially available materials, unless otherwise specified. The term "weight percent" may be denoted as "wt. %" herein.

All molecular weights as used herein are weight average molecular weights expressed as grams/mole, unless otherwise specified.

Herein, "comprising" means that other steps and other ingredients which do not affect the end result can be added. This term encompasses the terms "consisting of" and "consisting essentially of". The compositions and methods/processes of the present invention can comprise, consist of, and consist essentially of the essential elements and limitations of the invention described herein, as well as any of the additional or optional ingredients, components, steps, or limitations described herein.

The term "polymer" as used herein shall include materials whether made by polymerization of one type of monomer or made by two (i.e., copolymers) or more types of monomers.

The term "solid particle" as used herein means a particle that is not a liquid or a gas.

The term "water-soluble" as used herein, means that the material is soluble in water in the present composition. In general, the material should be soluble at 25° C. at a concentration of at least 0.1% by weight of the water solvent, preferably at least 1%, more preferably at least 5%, most preferably at least 15%.

The term "water-insoluble" as used herein, means that a material is not soluble in water in the present composition. Thus, the compound is not miscible with water.

Method for Treating the Appearance of Thinning Hair

The method herein comprises the steps of a) treating hair with an exfoliating shampoo composition comprising at least one chemical exfoliant; b) treating hair with a conditioner comprising at least one natural conditioning polymer and at least one natural stimulant; c) treating hair with a scalp serum comprising at least one vitamin, at least one natural extract, and salicylic acid.

Method of Treating Hair or Skin

The shampoo compositions of the present invention are used in a conventional manner for cleansing and conditioning hair or skin. Generally, a method of treating hair or skin of the present invention comprises applying the shampoo composition of the present invention to the hair or skin. More specifically, an effective amount of the shampoo composition is applied to the hair or skin, which has preferably been wetted with water, and then the shampoo composition is rinsed off. Such effective amounts generally range from about 1 g to about 50 g, preferably from about 1 g to about 20 g. Application to the hair typically includes working the composition through the hair such that most or all of the hair is contacted with the composition.

This method for treating the hair or skin comprises the steps of: (a) applying an effective amount of the shampoo composition to the hair or skin, and (b) rinsing the applied areas of hair or skin with water. These steps can be repeated as many times as desired to achieve the desired cleansing and conditioning benefit.

Regarding application of the serum, the composition should generally be applied via a spray applicator. The serum should be applied to hair at least twice, daily, but only after completing the shampooing and conditioning steps of the invention. The user should spray the composition on the scalp at least 10 to 20 times from a conventional pump sprayer, such that the entire scalp is covered. Treatment with the serum does not require that the user rinse with water after application.

Exfoliating Shampoo Composition

The shampoo compositions of the present invention comprise an anionic surfactant system. The anionic surfactant system is included to provide cleaning performance to the composition. The anionic surfactant system comprises at least one anionic surfactant, and optionally an amphoteric surfactant, a zwitterionic surfactant, a cationic surfactant, a nonionic surfactant, or a combination thereof. Such surfactants should be physically and chemically compatible with the essential components described herein, or should not otherwise unduly impair product stability, aesthetics, or performance.

Suitable anionic surfactant components for use in the shampoo composition herein include those that are known for use in hair care or other shampoo compositions. The concentration of the anionic surfactant system in the shampoo composition should be sufficient to provide the desired cleaning and lather performance, and generally ranges from about 5% to about 50%, preferably from about 8% to about 30%, more preferably from about 10% to about 25%, by weight of the composition.

Preferred anionic surfactants suitable for use in the shampoo compositions are alkyl sulfates and alkyl ether sulfates. These materials have the respective formulae $ROSO_3M$ and $RO(C_2H_4O)_xSO_3M$, wherein R is alkyl or alkenyl of from about 8 to about 18 carbon atoms, x is an integer having a value of from about 1 to about 10, and M is a cation such as ammonium, an alkanolamine such as triethanolamine, a monovalent metal such as sodium and potassium, or a polyvalent metal cation such as magnesium and calcium. Solubility of the surfactant will depend upon the particular anionic surfactants and cations chosen.

Preferably, R has from about 8 to about 18 carbon atoms, more preferably from about 10 to about 16 carbon atoms, even more preferably from about 12 to about 14 carbon atoms, in both the alkyl sulfates and alkyl ether sulfates. The alkyl ether sulfates are typically made as condensation products of ethylene oxide and monohydric alcohols having from about 8 to about 24 carbon atoms. The alcohols can be synthetic or they can be derived from fats, e.g., coconut oil, palm kernel oil, tallow. Lauryl alcohol and straight chain alcohols derived from coconut oil or palm kernel oil are preferred. Such alcohols are reacted with from about 0 to about 10, preferably from about 2 to about 5, more preferably about 3, molar proportions of ethylene oxide, and the resulting mixture of molecular species having, for example, an average of 3 moles of ethylene oxide per mole of alcohol is sulfated and neutralized.

Specific non-limiting examples of alkyl ether sulfates which may be used in the shampoo compositions of the present invention include sodium and ammonium salts of coconut alkyl triethylene glycol ether sulfate, tallow alkyl triethylene glycol ether sulfate, and tallow alkyl hexa-oxyethylene sulfate. Highly preferred alkyl ether sulfates are those comprising a mixture of individual compounds, wherein the compounds in the mixture have an average alkyl chain length of from about 10 to about 16 carbon atoms and an average degree of ethoxylation of from about 1 to about 4 moles of ethylene oxide. Such a mixture also comprises from about 0% to about 20% by weight $C_{12-13}$ compounds; from about 60% to about 100% by weight of $C_{14-15-16}$ compounds; from about 0% to about 20% by weight of $C_{17-18-19}$ compounds; from about 3% to about 30% by weight of compounds having a degree of ethoxylation of 0; from about 45% to about 90% by weight of compounds having a degree of ethoxylation from about 1 to about 4; from about 10% to about 25% by weight of compounds having a degree of ethoxylation from about 4 to about 8; and from about 0.1% to about 15% by weight of compounds having a degree of ethoxylation greater than about 8.

Another suitable class of anionic surfactants are the water-soluble salts of the organic, sulfuric acid reaction products of the general formula $R_1$—$SO_3$-M wherein $R_1$ is chosen from the group consisting of a straight or branched chain, saturated aliphatic hydro-carbon radical having from 8 to 24, preferably 12 to 18, carbon atoms; and M is a cation. Important examples are the salts of an organic sulfuric acid reaction product of a hydrocarbon of the methane series, including iso-, neo-, ineso-, and n-paraffins, having 8 to 24 carbon atoms, preferably 12 to 18 carbon atoms, and a sulfonating agent e.g., $SO_3$, $H_2SO_4$, oleum, obtained according to known sulfonation methods, including bleaching and hydrolysis. Preferred are alkali metal and ammonium sulfonated $C_{12-18}$-n-paraffins.

Examples of anionic surfactants for use in the shampoo compositions include ammonium lauryl sulfate, ammonium laureth sulfate, triethylamine lauryl sulfate, triethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, sodium lauryl sulfate, sodium laureth sulfate, potassium lauryl sulfate, potassium laureth sulfate, sodium lauryl sarcosinate, sodium lauroyl sarcosinate, lauryl sarcosine, cocoyl sarcosine, ammonium cocoyl sulfate, ammonium lauroyl sulfate, sodium cocoyl sulfate, sodium lauroyl sulfate, potassium cocoyl sulfate, potassium lauryl sulfate, triethanolamine lauryl sulfate, triethanolamine lauryl sulfate, monoethanolamine cocoyl sulfate, monoethanolamine lauryl sulfate, and combinations thereof.

Still other suitable anionic surfactants are the reaction products of fatty acids esterified with isethionic acid and neutralized with sodium hydroxide where, for example, the fatty acids are derived from coconut oil or palm kernel oil, and sodium or potassium salts of fatty acid amides of methyl tauride where, for example, the fatty acids are derived from coconut oil or palm kernel oil.

Other anionic surfactants suitable for use in the shampoo compositions are the succinnates, examples of which include disodium N-octadecylsulfosuccinnate, disodium lauryl sulfosuccinate, diammonium lauryl sulfosuccinate, tetrasodium N-(1,2-dicarboxyethyl)-N-octadecylsulfosuccinnate, diamyl ester of sodium sulfosuccinic acid, dihexyl ester of sodium sulfosuccinic acid, and dioctyl esters of sodium sulfosuccinic acid. Particularly preferred is disodium laureth sulfosuccinate.

Other suitable anionic surfactants include olefin sulfonates having about 10 to about 24 carbon atoms. In this context, the term "olefin sulfonates" refers to compounds which can be produced by the sulfonation of alpha-olefins by means of uncomplexed sulfur trioxide, followed by neutralization of the acid reaction mixture in conditions such that any sulfones which have been formed in the reaction are hydrolyzed to give the corresponding hydroxy-alkanesulfonates. The alpha-olefins from which the olefin sulfonates are derived are mono-olefins having from about 10 to about 24 carbon atoms, preferably from about 12 to about 16 carbon atoms. Preferably, they are straight chain olefins.

Another class of anionic surfactants suitable for use herein is the beta-alkyloxy alkane sulfonates. These surfactants conform to the formula:

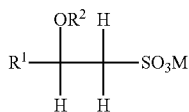

where $R^1$ is a straight chain alkyl group having from about 6 to about 20 carbon atoms, $R^2$ is a lower alkyl group having from about 1 to about 3 carbon atoms, preferably 1 carbon atom, and M is a water-soluble cation as described.

In addition to the sulfates, isethionates, sulfonates, sulfosuccinates described above, other potential anions for the anionic surfactant include phosphonates, phosphates, and carboxylates.

The shampoo compositions of the present invention may also include one or more additional surfactants selected from the group consisting of amphoteric surfactants, zwitterionic surfactants, cationic surfactants, and nonionic surfactants. Suitable amphoteric, zwitterionic, cationic, or nonionic surfactants for use in the shampoo compositions herein include those which are known for use in hair care or other shampoo compositions. The concentration of such surfactants preferably ranges from about 0.5% to about 20%, preferably from about 1% to about 10%, by weight of the composition. Non-limiting examples of suitable surfactants are described in U.S. Pat. Nos. 5,104,646 and 5,106,609, both to Bolich, Jr. et al.

Non-limiting examples of other surfactants suitable for use in the shampoo compositions are described in McCutcheon's, Emulsifiers and Detergents, 1989 Annual, published by M. C. Publishing Co.

Chemical Exfoliant

The shampoo composition includes at least one chemical exfoliant. The exfoliant is included in order to remove dead skin and expose hair follicles in preparation for delivery of treatment actives herein. Non-limiting chemical exfoliants include salicylic acid, glycolic acid, enzymes, citric acid, malic acid, alpha hydroxyl acid (AHA's), beta hydroxyl acid, (BHA's) and mixtures thereof.

The chemical exfoliant may be present in the shampoo composition at a level of from about 0.050% to about 10.0%, preferably from about 0.100% to about 8.00%, and most preferably from about 0.500% to about 5.00% by weight of the composition.

Oily Conditioning Agent

In a preferred embodiment of the present invention, the shampoo compositions comprise one or more oily conditioning agents. Oily conditioning agents include materials which are used to give a particular conditioning benefit to hair and/or skin. In hair treatment compositions, suitable conditioning agents are those which deliver one or more benefits relating to shine, softness, combability, antistatic properties, wet-handling, damage, manageability, body, and greasiness. The oily conditioning agents useful in the compositions of the present invention typically comprise a water-insoluble, water-dispersible, non-volatile, liquid that forms emulsified, liquid particles. Suitable oily conditioning agents for use in the composition are those conditioning agents characterized generally as silicones (e.g., silicone oils, cationic silicones, silicone gums, high refractive silicones, and silicone resins), organic conditioning oils (e.g., hydrocarbon oils, polyolefins, and fatty esters) or combinations thereof, or those conditioning agents which otherwise form liquid, dispersed particles in the aqueous surfactant matrix herein.

One or more oily conditioning agents are typically present at a concentration from about 0.01% to about 10%, preferably from about 0.1% to about 8%, more preferably from about 0.2% to about 4%, by weight of the composition.

Silicone Conditioning Agent

The oily conditioning agents of the compositions of the present invention are preferably a water-insoluble silicone conditioning agent. The silicone conditioning agent may comprise volatile silicone, non-volatile silicone, or combinations thereof. Preferred are non-volatile silicone conditioning agents. If volatile silicones are present, it will typically be incidental to their use as a solvent or carrier for commercially available forms of non-volatile silicone materials ingredients, such as silicone gums and resins. The silicone conditioning agent particles may comprise a silicone fluid conditioning agent and may also comprise other ingredients, such as a silicone resin to improve silicone fluid deposition efficiency or enhance glossiness of the hair.

Non-limiting examples of suitable silicone conditioning agents, and optional suspending agents for the silicone, are described in U.S. Reissue Pat. No. 34,584, U.S. Pat. No. 5,104,646, and U.S. Pat. No. 5,106,609. The silicone conditioning agents for use in the compositions of the present invention preferably have a viscosity, as measured at 25° C., from about 20 to about 2,000,000 centistokes ("csk"), more preferably from about 1,000 to about 1,800,000 csk, even more preferably from about 5,000 to about 1,500,000 csk, more preferably from about 10,000 to about 1,000,000 csk.

In an opaque composition embodiment of the present invention, the shampoo composition comprises a non-volatile silicone oil having a particle size as measured in the shampoo composition from about 1 µm to about 50 µm. In an embodiment of the present invention for small particle application to the hair, the shampoo composition comprises a non-volatile silicone oil having a particle size as measured in the shampoo composition from about 100 nm to about 1 µm. A substantially clear composition embodiment of the present invention comprises a non-volatile silicone oil having a particle size as measured in the shampoo composition of less than about 100 nm.

Non-volatile silicone oils suitable for use in compositions of the present invention may be selected from organo-modified silicones and fluoro-modified silicones. In one embodiment of the present invention, the non-volatile silicone oil is an organo-modified silicone which comprises an organo group selected from the group consisting of alkyl groups, alkenyl groups, hydroxyl groups, amine groups, quaternary groups, carboxyl groups, fatty acid groups, ether groups, ester groups, mercapto groups, sulfate groups, sulfonate groups, phosphate groups, propylene oxide groups, and ethylene oxide groups.

In a preferred embodiment of the present invention, the non-volatile silicone oil is dimethicone.

Background material on silicones including sections discussing silicone fluids, gums, and resins, as well as manufacture of silicones, are found in *Encyclopedia of Polymer Science and Engineering*, vol. 15, 2d ed., pp 204-308, John Wiley & Sons, Inc. (1989).

Silicone fluids suitable for use in the compositions of the present invention are disclosed in U.S. Pat. No. 2,826,551, U.S. Pat. No. 3,964,500, U.S. Pat. No. 4,364,837, British Pat. No. 849,433, and *Silicon Compounds*, Petrarch Systems, Inc. (1984).

Organic Conditioning Oils

The oily conditioning agent of the compositions of the present invention may also comprise at least one organic conditioning oil, either alone or in combination with other conditioning agents, such as the silicones described above.

Hydrocarbon Oils

Suitable organic conditioning oils for use as conditioning agents in the compositions of the present invention include, but are not limited to, hydrocarbon oils having at least about 10 carbon atoms, such as cyclic hydrocarbons, straight chain aliphatic hydrocarbons (saturated or unsaturated), and branched chain aliphatic hydrocarbons (saturated or unsaturated), including polymers and mixtures thereof. Straight chain hydrocarbon oils preferably are from about $C_{12}$ to about $C_{19}$. Branched chain hydrocarbon oils, including hydrocarbon polymers, typically will contain more than 19 carbon atoms.

Specific non-limiting examples of these hydrocarbon oils include paraffin oil, mineral oil, saturated and unsaturated dodecane, saturated and unsaturated tridecane, saturated and unsaturated tetradecane, saturated and unsaturated pentadecane, saturated and unsaturated hexadecane, polybutene, polydecene, and mixtures thereof. Branched-chain isomers of these compounds, as well as of higher chain length hydrocarbons, can also be used, examples of which include 2,2,4,4,6,6,8,8-dimethyl-10-methylundecane and 2,2,4,4,6,6-dimethyl-8-methylnonane, available from Permethyl Corporation. A preferred hydrocarbon polymer is polybutene, such as the copolymer of isobutylene and butene, which is commercially available as L-14 polybutene from Amoco Chemical Corporation.

Polyolefins

Organic conditioning oils for use in the compositions of the present invention can also include liquid polyolefins, more preferably liquid poly-α-olefins, more preferably hydrogenated liquid poly-α-olefins. Polyolefins for use herein are prepared by polymerization of $C_4$ to about $C_{14}$ olefenic monomers, preferably from about $C_6$ to about $C_{12}$.

Non-limiting examples of olefenic monomers for use in preparing the polyolefin liquids herein include ethylene, propylene, 1-butene, 1-pentene, 1-hexene, 1-octene, 1-decene, 1-dodecene, 1-tetradecene, branched chain isomers such as 4-methyl-1-pentene, and mixtures thereof. Also suitable for preparing the polyolefin liquids are olefin-containing refinery feedstocks or effluents.

Fatty Esters

Other suitable organic conditioning oils for use as the conditioning agent in the compositions of the present invention include fatty esters having at least 10 carbon atoms. These fatty esters include esters with hydrocarbyl chains derived from fatty acids or alcohols. The hydrocarbyl radicals of the fatty esters hereof may include or have covalently bonded thereto other compatible functionalities, such as amides and alkoxy moieties (e.g., ethoxy or ether linkages, etc.).

Specific examples of preferred fatty esters include, but are not limited to, iso-propyl isostearate, hexyl laurate, isohexyl laurate, isohexyl palmitate, isopropyl palmitate, decyl oleate, isodecyl oleate, hexadecyl stearate, decyl stearate, isopropyl isostearate, dihexyldecyl adipate, lauryl lactate, myristyl lactate, cetyl lactate, oleyl stearate, oleyl oleate, oleyl myristate, lauryl acetate, cetyl propionate, and oleyl adipate.

Other fatty esters suitable for use in the compositions of the present invention are those known as polyhydric alcohol esters. Such polyhydric alcohol esters include alkylene glycol esters.

Still other fatty esters suitable for use in the compositions of the present invention are glycerides, including, but not limited to, mono-, di-, and tri-glycerides, preferably di- and tri-glycerides, more preferably triglycerides. A variety of these types of materials can be obtained from vegetable and animal fats and oils, such as castor oil, safflower oil, cottonseed oil, corn oil, olive oil, cod liver oil, almond oil, avocado oil, palm oil, sesame oil, lanolin and soybean oil. Synthetic oils include, but are not limited to, triolein and tristearin glyceryl dilaurate.

Fluorinated Conditioning Compounds

Fluorinated compounds suitable for delivering conditioning to hair or skin as organic conditioning oils include perfluoropolyethers, perfluorinated olefins, fluorine based specialty polymers that may be in a fluid or elastomer form similar to the silicone fluids previously described, and perfluorinated dimethicones. Specific non-limiting examples of suitable fluorinated compounds include the Fomblin product line from Ausimont which includes HC/04, HC/25, HC01, HC/02, HC/03; Dioctyldodecyl Fluoroeptyl Citrate, commonly called Biosil Basics Fluoro Gerbet 3.5 supplied by Biosil Technologies; and Biosil Basics Fluorosil LF also supplied by Biosil Technologies.

Fatty Alcohols

Other suitable organic conditioning oils for use in the shampoo compositions of the present invention include, but are not limited to, fatty alcohols having at least about 10 carbon atoms, more preferably about 10 to about 22 carbon atoms, most preferably about 12 to about 16 carbon atoms. Also suitable for use in the shampoo compositions of the present inventions are alkoxylated fatty alcohols which conform to the general formula:

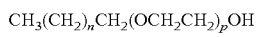

$$CH_3(CH_2)_nCH_2(OCH_2CH_2)_pOH$$

wherein n is a positive integer having a value from about 8 to about 20, preferably about 10 to about 14, and p is a positive integer having a value from about 1 to about 30, preferably from about 2 to about 23.

Alkyl Glucosides and Alkyl Glucoside Derivatives

Suitable organic conditioning oils for use in the shampoo compositions of the present invention include, but are not limited to, alkyl glucosides and alkyl glucoside derivatives. Specific non-limiting examples of suitable alkyl glucosides and alkyl glucoside derivatives include Glucam E-10, Glucam E-20, Glucam P-10, and Glucquat 125 commercially available from Amerchol.

Other Conditioning Agents

Quaternary Ammonium Compounds

Suitable quaternary ammonium compounds for use as conditioning agents in the shampoo compositions of the present invention include, but are not limited to, hydrophilic quaternary ammonium compounds with a long chain substituent having a carbonyl moiety, like an amide moiety, or a phosphate ester moiety or a similar hydrophilic moiety.

Examples of useful hydrophilic quaternary ammonium compounds include, but are not limited to, compounds designated in the CTFA Cosmetic Dictionary as ricinoleamidopropyl trimonium chloride, ricinoleamido trimonium ethylsulfate, hydroxy stearamidopropyl trimoniummethylsulfate and hydroxy stearamidopropyl trimonium chloride, or combinations thereof.

Examples of other useful quaternary ammonium surfactants include, but are not limited to, Quaternium-33, Quaternium-43, isostearamidopropyl ethyldimonium ethosulfate, Quaternium-22 and Quaternium-26, or combinations thereof, as designated in the CTFA Dictionary.

Other hydrophilic quaternary ammonium compounds useful in a composition of the present invention include, but are not limited to, Quaternium-16, Quaternium-27, Quaternium-30, Quaternium-52, Quaternium-53, Quaternium-56, Quaternium-60, Quaternium-61, Quaternium-62, Quaternium-63, Quaternium-71, and combinations thereof.

Polyethylene Glycols

Additional compounds useful herein as conditioning agents include polyethylene glycols and polypropylene glycols having a molecular weight of up to about 2,000,000 such as those with CTFA names PEG-200, PEG-400, PEG-600, PEG-1000, PEG-2M, PEG-7M, PEG-14M, PEG-45M and mixtures thereof.

Additional Components

The shampoo compositions of the present invention may further comprise one or more additional components known for use in hair care or shampoo products, provided that the additional components are physically and chemically compatible with the essential components described herein, or do not otherwise unduly impair product stability, aesthetics or performance. Individual concentrations of such additional components may range from about 0.001% to about 10% by weight of the shampoo compositions.

Non-limiting examples of additional components for use in the composition include natural cationic deposition polymers, synthetic cationic deposition polymers, anti-dandruff agents, particles, suspending agents, paraffinic hydrocarbons, propellants, viscosity modifiers, dyes, non-volatile solvents or diluents (water-soluble and water-insoluble), pearlescent aids, foam boosters, additional surfactants or nonionic cosurfactants, pediculocides, pH adjusting agents, perfumes, preservatives, chelants, proteins, skin active agents, sunscreens, UV absorbers, and vitamins.

Cellulose or Guar Cationic Deposition Polymers

The shampoo compositions of the present invention may also include cellulose or guar cationic deposition polymers. Cellulose or glactomannan cationic deposition polymers are preferred. Generally, such cellulose or guar cationic deposition polymers may be present at a concentration from about 0.05% to about 5%, by weight of the composition. Suitable cellulose or guar cationic deposition polymers have a molecular weight of greater than about 5,000. Preferably, the cellulose or guar cationic deposition polymers have a molecular weight of greater than about 200,000. Additionally, such cellulose or guar deposition polymers have a charge density from about 0.15 meq/g to about 4.0 meq/g at the pH of intended use of the shampoo composition, which pH will generally range from about pH 3 to about pH 9, preferably between about pH 4 and about pH 8. The pH of the compositions of the present invention are measured neat.

Suitable cellulose or guar cationic polymers include those which conform to the following formula:

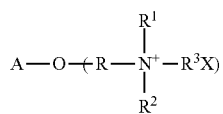

wherein A is an anhydroglucose residual group, such as a cellulose anhydroglucose residual; R is an alkylene oxyalkylene, polyoxyalkylene, or hydroxyalkylene group, or combination thereof; $R^1$, $R^2$, and $R^3$ independently are alkyl, aryl, alkylaryl, arylalkyl, alkoxyalkyl, or alkoxyaryl groups, each group containing up to about 18 carbon atoms, and the total number of carbon atoms for each cationic moiety (i.e., the sum of carbon atoms in $R^1$, $R^2$ and $R^3$) preferably being about 20 or less; and X is an anionic counterion. Non-limiting examples of such counterions include halides (e.g., chlorine, fluorine, bromine, iodine), sulfate and methylsulfate. The degree of cationic substitution in these polysaccharide polymers is typically from about 0.01 to about 1 cationic groups per anhydroglucose unit.

In one embodiment of the invention, the cellulose or guar cationic polymers are salts of hydroxyethyl cellulose reacted with trimethyl ammonium substituted epoxide, referred to in the industry (CTFA) as Polyquaternium 10 and available from Amerchol Corp. (Edison, N.J., USA).

Synthetic Cationic Deposition Polymers

The shampoo compositions of the present invention may also include synthetic cationic deposition polymers. Generally, such synthetic cationic deposition polymers may be present at a concentration from about 0.025% to about 5%, by weight of the composition. Such synthetic cationic deposition polymers have a molecular weight from about 1,000 to about 5,000,000. Additionally, such synthetic cationic deposition polymers have a charge density from about 0.1 meq/g to about 5.0 meq/g.

Suitable synthetic cationic deposition polymers include those which are water-soluble or dispersible, cationic, non-crosslinked, conditioning copolymers comprising: (i) one or more cationic monomer units; and (ii) one or more nonionic monomer units or monomer units bearing a terminal negative charge; wherein said copolymer has a net positive charge, a cationic charge density of from about 0.5 meq/g to about 10 meg/g, and an average molecular weight from about 1,000 to about 5,000,000.

Non-limiting examples of suitable synthetic cationic deposition polymers are described in United States Patent Application Publication US 2003/0223951 A1 to Geary et al.

Anti-Dandruff Actives

The compositions of the present invention may also contain an anti-dandruff active. Suitable non-limiting examples of anti-dandruff actives include pyridinethione salts, azoles, selenium sulfide, particulate sulfur, keratolytic agents, and mixtures thereof. Such anti-dandruff actives should be physically and chemically compatible with the essential components of the composition, and should not otherwise unduly impair product stability, aesthetics or performance.

Pyridinethione anti-microbial and anti-dandruff agents are described, for example, in U.S. Pat. No. 2,809,971; U.S. Pat. No. 3,236,733; U.S. Pat. No. 3,753,196; U.S. Pat. No. 3,761,418; U.S. Pat. No. 4,345,080; U.S. Pat. No. 4,323,683; U.S. Pat. No. 4,379,753; and U.S. Pat. No. 4,470,982.

Azole anti-microbials include imidazoles such as climbazole and ketoconazole.

Selenium sulfide compounds are described, for example, in U.S. Pat. No. 2,694,668; U.S. Pat. No. 3,152,046; U.S. Pat. No. 4,089,945; and U.S. Pat. No. 4,885,107.

Sulfur may also be used as a particulate anti-microbial/anti-dandruff agent in the anti-microbial compositions of the present invention.

The present invention may further comprise one or more keratolytic agents such as salicylic acid. In a preferred embodiment, salicylic acid provides chemical exfoliation activity.

Additional anti-microbial actives of the present invention may include extracts of melaleuca (tea tree) and charcoal.

When present in the composition, the anti-dandruff active is included in an amount from about 0.01% to about 5%, preferably from about 0.1% to about 3%, and more preferably from about 0.3% to about 2%, by weight of the composition.

Particles

The compositions of the present invention optionally may comprise particles. Preferably, particles useful in the present invention are dispersed water-insoluble particles. Particles useful in the present invention can be inorganic, synthetic, or semi-synthetic. In the compositions of the present invention, it is preferable to incorporate no more than about 20%, more preferably no more than about 10% and even more preferably no more than 2%, by weight of the composition, of particles. In an embodiment of the present invention, the particles have an average mean particle size of less than about 300 μm.

Non-limiting examples of inorganic particles include colloidal silicas, fumed silicas, precipitated silicas, silica gels, magnesium silicate, glass particles, talcs, micas, sericites, and various natural and synthetic clays including bentonites, hectorites, and montmorillonites.

Examples of synthetic particles include silicone resins, poly(meth)acrylates, polyethylene, polyester, polypropylene, polystyrene, polyurethane, polyamide (e.g., Nylon®), epoxy resins, urea resins, acrylic powders, and the like.

Non-limiting examples of hybrid particles include sericite & crosslinked polystyrene hybrid powder, and mica and silica hybrid powder.

Opacifying Agents

The compositions of the present invention may also contain one or more opacifying agents. Opacifying agents are typically used in cleansing compositions to impart desired aesthetic benefits to the composition, such as color or pearlescence. In the compositions of the present invention, it is preferable to incorporate no more than about 20%, more preferably no more than about 10% and even more preferably no more than 2%, by weight of the composition, of opacifying agents.

Suitable opacifying agents include, for example, fumed silica, polymethylmethacrylate, micronized Teflon®, boron nitride, barium sulfate, acrylate polymers, aluminum silicate, aluminum starch octenylsuccinate, calcium silicate, cellulose, chalk, corn starch, diatomaceous earth, Fuller's earth, glyceryl starch, hydrated silica, magnesium carbonate, magnesium hydroxide, magnesium oxide, magnesium trisilicate, maltodextrin, microcrystalline cellulose, rice starch, silica, titanium dioxide, zinc laurate, zinc myristate, zinc neodecanoate, zinc rosinate, zinc stearate, polyethylene, alumina, attapulgite, calcium carbonate, calcium silicate, dextran, nylon, silica silylate, silk powder, soy flour, tin oxide, titanium hydroxide, trimagnesium phosphate, walnut shell powder, or mixtures thereof. The above mentioned powders may be surface treated with lecithin, amino acids, mineral oil, silicone oil, or various other agents either alone or in combination, which coat the powder surface and render the particles hydrophobic in nature.

The opacifying agents may also comprise various organic and inorganic pigments. The organic pigments are generally various aromatic types including azo, indigoid, triphenylmethane, anthraquinone, and xanthine dyes. Inorganic pigments include iron oxides, ultramarine and chromium or chromium hydroxide colors, and mixtures thereof.

Suspending Agents

The compositions of the present invention may further comprise a suspending agent at concentrations effective for suspending water-insoluble material in dispersed form in the compositions or for modifying the viscosity of the composition. Such concentrations generally range from about 0.1% to about 10%, preferably from about 0.3% to about 5.0%, by weight of the composition, of suspending agent.

Suspending agents useful herein include anionic polymers and nonionic polymers. Useful herein are vinyl polymers such as cross linked acrylic acid polymers with the CTFA name Carbomer.

Paraffinic Hydrocarbons

The compositions of the present invention may contain one or more paraffinic hydrocarbons. Paraffinic hydrocarbons suitable for use in compositions of the present invention include those materials which are known for use in hair care or other shampoo compositions, such as those having a vapor pressure at 1 atm of equal to or greater than about 21° C. (about 70° F.). Non-limiting examples include pentane and isopentane.

Propellants

The composition of the present invention also may contain one or more propellants. Propellants suitable for use in compositions of the present invention include those materials which are known for use in hair care or other shampoo compositions, such as liquefied gas propellants and compressed gas propellants. Suitable propellants have a vapor pressure at 1 atm of less than about 21° C. (about 70° F.). Non-limiting examples of suitable propellants are alkanes, isoalkanes, haloalkanes, dimethyl ether, nitrogen, nitrous oxide, carbon dioxide, and mixtures thereof.

Other Optional Components

The compositions of the present invention may contain fragrance.

The compositions of the present invention may also contain water-soluble and water-insoluble vitamins such as vitamins B1, B2, B6, B12, C, pantothenic acid, pantothenyl ethyl ether, panthenol, biotin and their derivatives, and vitamins A, D, E, and their derivatives. The compositions of the present invention may also contain water-soluble and water-insoluble amino acids such as asparagine, alanine, indole, glutamic acid and their salts, and tyrosine, tryptamine, lysine, histadine and their salts.

The compositions of the present invention may contain a mono- or divalent salt such as sodium chloride.

The compositions of the present invention may also contain chelating agents.

The compositions of present invention may further comprise materials useful for hair loss prevention and hair growth stimulants or agents.

Conditioner

The conditioner is applied to the hair and scalp after treatment with the shampoo composition according to the method herein.

The conditioner composition comprises one or more conditioning actives. Preferably, the actives are natural or naturally derived actives selected from starches, guars, non-guar galactomannan polymer derivatives, plant extracts, and the like.

Starches suitable for the conditioner compositions are those which generally result from any vegetable source. Non-limiting examples include corn, potato, the oats, rice, tapioca, the sorghum, the barley or corn.

The conditioning actives are used preferably in an amount of from 0.01 to 20% in weight compared to the total weight of the composition. More preferably, from 0.05 to 15% in weight compared to the total weight of the conditioner composition and even more preferably from 0.1 to 10% by weight of the composition.

The hair conditioning compositions may also comprise non-guar galactomannan polymer derivatives having a mannose to galactose ratio of greater than 2:1 on a monomer to monomer basis, the non-guar galactomannan polymer derivative is selected from the group consisting of a cationic non-guar galactomannan polymer derivative and an amphoteric non-guar galactomannan polymer derivative having a net positive charge. As used herein, the term "cationic non-guar galactomannan" refers to a non-guar galactomannan polymer to which a cationic group is added. The term "amphoteric non-guar galactomannan" refers to a non-guar galactomannan polymer to which a cationic group and an anionic group are added such that the polymer has a net positive charge. Non-guar galactomannan polymer derivatives provide improved efficacy of conditioning agents. Enhanced conditioning benefits include increased silicone deposition, which results in improved hair smoothness and combability. Further, the non-guar galactomannan polymer derivatives have been found to reduce overall viscosity of conditioning compositions, which results in improved feel benefits.

The gum for use in preparing the non-guar galactomannan polymer derivatives is typically obtained as naturally occurring material such as seeds or beans from plants. Examples of various non-guar galactomannan polymers include but are not limited to Tara gum (3 parts mannose/1 part galactose), Locust bean or carob (4 parts mannose/1 part galactose), and *cassia* gum (5 parts mannose/1 part galactose). A preferred non-guar galactomannan polymer derivative is cationic *cassia*.

The cationic non-guar galactomannan polymer derivatives have a molecular weight from about 1,000 to about 10,000,000. In one embodiment of the present invention, the cationic non-guar galactomannan polymer derivatives have a molecular weight from about 5,000 to about 3,000,000. As used herein, the term "molecular weight" refers to the weight average molecular weight. The weight average molecular weight may be measured by gel permeation chromatography.

The hair conditioning compositions of the present invention may include non-guar galactomannan polymer derivatives which have a cationic charge density from about 0.7 meq/g to about 7 meq/g. In one embodiment of the present invention, the non-guar galactomannan polymer derivatives have a charge density from about 0.9 meq/g to about 7 meq/g. The degree of substitution of the cationic groups onto the non-guar galactomannan structure should be sufficient to provide the requisite cationic charge density.

In one embodiment of the present invention, the non-guar galactomannan polymer derivative is a cationic derivative of the non-guar galactomannan polymer, which is obtained by reaction between the hydroxyl groups of the non-guar galactomannan polymer and reactive quaternary ammonium compounds In another embodiment of the present invention, the non-guar galactomannan polymer derivative is an amphoteric non-guar galactomannan polymer derivative having a net positive charge, obtained when the cationic non-guar galactomannan polymer derivative further comprises an anionic group.

The hair conditioning compositions may comprise non-guar galactomannan polymer derivatives at a range of from about 0.01% to about 10%, and more preferably from about 0.05% to about 5%, by weight of the composition.

The conditioner compositions may further include one or more conditioning polymers selected from derivatives of cellulose ethers, quaternary derivatives of guar, homopolymers and copolymers of DADMAC, homopolymers and copolymers of MAPTAC and quaternary derivatives of starches. Specific examples, using the CTFA designation, include, but are not limited to Polyquaternium-10, Guar hydroxypropyltrimonium chloride, Starch hydroxypropyltrimonium chloride, Polyquaternium-4, Polyquaternium-5, Polyquaternium-6, Polyquaternium-7, Polyquaternium-14, Polyquaternium-15, Polyquaternium-22, Polyquaternium-24, Polyquaternium-28, Polyquaternium-32, Polyquaternium-33, Polyquaternium-36, Polyquaternium-37, Polyquaternium-39, Polyquaternium-45, Polyquaternium-47 and polymethacrylamidopropyltrimonium chloride, and mixtures thereof. When used, the conditioning polymers are preferably included in the conditioner composition of this invention at a concentration of from 0.1 to 10 weight percent, preferably from 0.2 to 6 weight percent and most preferably from 0.2 to 5 weight percent.

Conditioning Agents

The conditioning compositions may also comprise one or more conditioning agents, such as those selected from the group consisting of cationic surfactants, cationic polymers, nonvolatile silicones (including soluble and insoluble silicones), nonvolatile hydrocarbons, saturated C14 to C22 straight chain fatty alcohols, nonvolatile hydrocarbon esters, and mixtures thereof. Preferred conditioning agents are cationic surfactants, cationic polymers, saturated C14 to C22 straight chain fatty alcohols, quarternary ammonium salts and silicones (especially insoluble silicones). Plant extracts such as ginseng root extract, *silybaum marianum* extract, *phyllanthus emblica* fruit extract, and the like are also suitable. The components hereof can comprise from about 0.1% to about 99%, more preferably from about 0.5% to about 90%, of conditioning agents. However, in the presence of an aqueous carrier, the conditioning agents preferably comprise from about 0.1% to about 90%, more preferably from about 0.5 to about 60% and most preferably from about 1% to about 50% by weight of the hair conditioning composition.

The conditioning compositions also include one or more natural stimulants in order to stimulate the scalp prior to application of the serum component. Exemplary natural stimulants include those such as ginseng and caffeine.

Cationic Surfactants

Cationic surfactants, useful in the conditioner compositions, contain amino or quaternary ammonium moieties. The cationic surfactant will preferably, though not necessarily, be insoluble in the compositions hereof. Cationic surfactants among those useful herein are disclosed in the following documents: M.C. Publishing Co., McCutcheoris, Detergents Sc Emulsifiers, (North American edition 1979); Schwartz, et al., Surface Active Agents, Their Chemistry and Technology, New York: Interscience Publishers, 1949; U.S. Pat. No. 3,155, 591, Hilfer, issued Nov. 3, 1964; U.S. Pat. No. 3,929,678, Laughlin et al., issued Dec. 30, 1975; U.S. Pat. No. 3,959,461, Bailey et al., issued May 25, 1976; and U.S. Pat. No. 4,387, 090, Bolich, Jr., issued Jun. 7, 1983. Among the quaternary ammonium-containing cationic surfactant materials useful herein are those of the general formula:

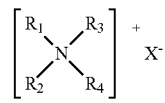

wherein R1-R4 are independently an aliphatic group of from about 1 to about 22 carbon atoms or an aromatic, alkoxy, polyoxyalkylene, alkylamido, hydroxyalkyl, aryl or alkylaryl group having from about 1 to about 22 carbon atoms; and X is a salt-forming anion such as those selected from halogen, (e.g. chloride, bromide), acetate, citrate, lactate, glycolate, phosphate nitrate, sulfate, and alkylsulfate radicals. The aliphatic groups may contain, in addition to carbon and hydrogen atoms, ether linkages, and other groups such as amino groups. The longer chain aliphatic groups, e.g., those of about 12 carbons, or higher, can be saturated or unsaturated. Especially preferred are di-long chain (e.g., di C12-22, preferably C14-C20, aliphatic, preferably alkyl) di-short chain (e.g., C1-C3 alkyl, preferably C1-C2 alkyl) and quaternary ammonium salts. Salts of primary, secondary and tertiary fatty amines are also suitable cationic surfactant materials. The alkyl groups of such amines preferably have from about 12 to about 22 carbon atoms, and may be substituted or unsubstituted. Such amines, useful herein, include stearamido propyl dimethyl amine, diethyl amino ethyl stearamide, dimethyl stearamine, dimethyl soyamine, soyamine, myristyl amine, tridecyl amine, ethyl stearylamine, N-tallowpropane diamine, ethoxylated (with 5 moles of ethylene oxide) stearylamine, dihydroxy ethyl stearylamine, and arachidylbehenylamine. Suitable amine salts include the halogen, acetate, phosphate, nitrate, citrate, lactate, and alkyl sulfate salts. Such salts include stearylamine hydrochloride, soyamine chloride, stearylamine formate, N-tallowpropane diamine dichloride and stearamidopropyl dimethylamine citrate. Cationic amine surfactants included among those useful in the present invention are disclosed in U.S. Pat. No. 4,275,055, Nachtigal, et al., issued Jun. 23, 1981. Cationic surfactants are preferably utilized at levels of from about 0.1% to about 10%, more preferably from about 0.25% to about 5%, most preferably from about 0.5% to about 2%, by weight of the composition.

Scalp Serum

The scalp serum is applied after treatment with the conditioner composition discussed hereinbefore.

The scalp serum compositions comprise a skin active agent in an amount sufficient to provide the desired skin active effect. The skin active agent or agents within the composition may be in the form of a solubilized or dispersed liquid, or in the form of a solubilized or dispersed solid.

The skin active agent in the scalp serum compositions and methods of the present invention are formulated with the composition at a variety of concentrations, but will generally represent from about 0.005% to about 20%, more typically from about 0.01% to about 10%, even more typically from about 0.05% to about 7%, by weight of the scalp serum composition. The concentration will vary depending upon factors such as the established safe and effective concentrations for the particular skin active agent selected, the degree or type of skin active benefit sought, and so forth. Non limiting examples of skin active agents suitable for use in the composition include anti-dandruff actives, steroidal anti-inflammatory agents (e.g., hydrocortisone), non-steroidal anti-inflammatory agents, anti-irritation actives, pediculocides or insecticides (e.g. for control of lice, fleas, ticks or other insects), vegetable based phytosterols and their derivatives (e.g., beta-sitosterol, campesterol, stigmasterol), cooling or other skin sensates, antimicrobial agents other than anti-dandruff actives, anesthetics, anti-histamines, astringents, enzymes, vitamins, hair growth actives, sunscreens, and other similar known or otherwise effective topical pharmaceutical or non-pharmaceutical active.

The scalp serum includes at least one natural extract. Exemplary natural extracts include those such as rosemary leaf extract, ginseng root extract, green tea leaf extract, yeast extract, *saccharomyces* lysate extract, *chlorella vulgaris* extract, licorice extract, turmeric root extract, hydrocotyl extract, and the like.

Non-limiting examples of suitable pediculocides include peperonyl butoxide, pyrethrum extract, imidacloprid topical solution, lindane (gammabenzene hexachloride), organophosphates (malathion), natural pyrethrins, synthetic pyrethroids (e.g., permethrin) and any other known or otherwise effective agent for controlling or treating skin, hair or fur against insects such as fleas, lice and other insects.

Non-limiting examples of skin active enzymes for use herein include oxidoreductases, transferases, lyases, hydrolases, isomerases, ligases, and similar other enzymes.

The skin active agent can include selected soothing anti-inflammatory actives at concentrations ranging from about 0.01% to about 5.0%, more preferably from about 0.05% to about 3.0%, by weight of the scalp serum composition. In this context, the soothing anti-inflammatory actives refer to any material other than steroidal anti-inflammatory agents that help to sooth and reduce skin irritation. Non-limiting examples of such actives include pantothenic acid derivatives, pantothenic ether, allantoin, or combinations thereof, preferably an alcohol derivative of pantothenic acid such as panthenol (including d-panthenol and 1-panthenol), some examples of which are described in CTFA Cosmetic Ingredient Handbook, The Cosmetic, Toiletry and Fragrance Association. Inc. pp. 272 273, 1992. Panthenol can also be used as a humectant, and shall be considered as a humectant for purposes of defining the compositions of the present invention when such compositions have no other humectants present. Especially preferred are allantoin, Vitamin E oil, and combinations thereof.

The skin active agent is preferably an anti-microbial active, most typically an antimicrobial anti-dandruff active, concentrations of which within the compositions range from about 0.001% to about 5%, more preferably from about 0.01% to about 3%, even more preferably from about 0.05% to about 1%, by weight of the composition. Preferred antimicrobial anti-dandruff actives include antifungal actives such as pyrithione salts, octopirox, ketoconazole, climbazole, ciclopirox, terbinafine, itraconazole and sulfur or sulfur-containing actives such as selenium sulfide. Preferred is zinc pyrithione (ZPT). And most preferred is salicylic acid at concentrations ranging from 0.005% to 2%, more preferably from about 0.005% to about 0.5%, by weight of the composition.

Selenium sulfide is a preferred antimicrobial anti-dandruff active for use in the compositions, effective concentrations of which range from about 0.001% to about 5.0%, preferably from about 0.01% to about 2.5%, more preferably from about 0.05% to about 1.0%, by weight of the scalp serum compositions. Selenium sulfide is generally regarded as a compound having one mole of selenium and two moles of sulfur, although it may also be a cyclic structure, $Se_xS_y$, wherein x+y=8. Selenium sulfides are well known in the personal care arts and are described, for example, in U.S. Pat. No. 2,694,668; U.S. Pat. No. 3,152,046; U.S. Pat. No. 4,089,945; and U.S. Pat. No. 4,885,107, which descriptions are incorporated herein by reference.

Other sulfur or sulfur-containing materials may also be used as the antimicrobial active in the scalp serum compositions, concentrations of which generally range from about 0.001% to about 5.0%, preferably from about 0.1% to about 5.0%, more preferably from about 1.0% to about 5.0%, by weight of the scalp serum composition.

Pyrithione antimicrobial actives, especially 1-hydroxy-2-pyridinethione salts, are highly preferred anti-dandruff actives for use in the scalp serum compositions. Preferred pyrithione salts are those formed from heavy metals such as zinc, tin, cadmium, magnesium, aluminum and zirconium. Zinc salts are most preferred, especially the zinc salt of 1-hydroxy-2-pyrithione (zinc pyrithione, ZPT). Other cations such as sodium may also be suitable. Particularly preferred are 1-hydroxy-2-pyrithione salts in platelet particle form, wherein the particles have an average size of up to about 20 microns, preferably up to about 8 microns, most preferably up to about 5 microns. Pyrithione antimicrobial active are well known in the hair care art and are described, for example, in U.S. Pat. No. 2,809,971; U.S. Pat. No. 3,236,733; U.S. Pat. No. 3,753,196; U.S. Pat. No. 3,761,418; U.S. Pat. No. 4,345,080; U.S. Pat. No. 4,323,683; U.S. Pat. No. 4,379,753; and U.S. Pat. No. 4,470,982, which descriptions are incorporated herein by reference.

Other specific examples of zinc-containing skin active agents for use in the compositions and methods of the present invention include zinc pyrithione, zinc acetate, zinc acetylmethionate, zinc aspartate, zinc borate, zinc carbonate, zinc chloride, zinc citrate, zinc DNA, zinc formaldehyde sulfoxylate, zinc gluconate, zinc glutamate, zinc hydrolyzed collagen, zinc lactate, zinc laurate, zinc myristate, zinc neodecanoate, zinc palmitate, zinc PCA, zinc pentadecene tricarboxylate, zinc ricinoleate, zinc ricinoleate, zinc rosinate, zinc stearate, zinc sulfate, zinc undecylenate, zinc oxide, zinc lactobionate, and combinations thereof.

The skin active agent for use in the composition and methods of the of the present invention can include any material that when added to the composition provides hair growth regulation (also referred to herein as "hair growth actives"). In this context, the term "hair growth regulation" includes stimulating hair growth; stimulating hair thickening; preventing, reducing, arresting and/or retarding the loss of hair; preventing, reducing, arresting and/or retarding the thinning of hair; increasing the rate of hair growth; inducing the formation of a greater number of hair strands; increasing the diameter of the hair strand; lengthening the hair strand; changing the hair follicle from vellus follicle to terminal follicle; inducing the formation of vellus follicles; converting follicles from telogen to anagen phase (thereby increasing the overall ratio of anagen phase follicles relative to telogen phase follicles); advancing a follicle from an earlier stage of anagen to a later stage of anagen; reducing the conversion from anagen to catagen phase; treating alopecia; and any combination thereof.

Preferred hair growth actives include zinc-containing salts such as those described herein, especially zinc lactobionate. Other hair growth actives suitable for use in the compositions and methods of the present invention include those described in U.S. Pat. No. 6,124,362 (Bradbury et al.), which description is incorporated herein by reference.

Volatile Liquid

The scalp serum compositions of the present invention may comprise a volatile liquid carrier suitable for topical application to human skin. These liquid carriers include any liquid that is volatile under ambient conditions, or any combination of liquid carriers which combination is volatile under ambient conditions, and which is otherwise suitable for topical application to the scalp or other area of the skin.

The volatile liquid carrier or combination of carriers in the scalp tonic compositions of the present invention represent from about 40% to about 99%, preferably from about 50% to about 80%, more preferably from about 55% to about 80%, and even more preferably from about 60% to about 75%, by weight of the scalp serum composition.

The volatile liquid carrier preferably comprises a monohydric alcohol having from 2 to 8 carbon atoms, more preferably from about 2 to 4 carbon atoms, preferred examples of which include ethanol, isopropanol, propanol, n-butanol, t-butanol, isobutanol, and combinations thereof. Most preferred is ethanol. Other volatile liquid carriers can also be used in the composition, preferably non-silicone-containing liquid carriers, either alone or in various combinations such as in combination with the preferred monohydric alcohols described herein. Non-limiting examples of such other volatile liquid carriers include volatile hydrocarbon liquids, polyhydric alcohols, esters or ethers of monohydric or polyhydric alcohols, silicones, and so forth, provided that such other volatile liquid carrier has the requisite volatility as described herein, and provided that such other volatile liquid carrier is not also the liquid humectant component of the composition as described hereinafter.

Moisturizing Material

The scalp serum compositions of the present invention may comprise one or more moisturizing materials to provide the composition with improved moisturization and/or flake reduction benefits. The moisturizing material can be any material known or otherwise effective in providing skin moisturization and is preferably limited to those materials that provide the composition with the Scalp Moisturization or Instant Flake Reduction values as described herein.

The moisturizing material for use in the scalp serum compositions of the present invention is preferably a liquid humectant. Suitable humectants include any liquid hygroscopic material that is known for or otherwise effective in providing skin moisturization from a leave-on composition. Concentrations of such materials will vary depending factors such as the formulation selected and the particular humectant within the formulation, but such concentrations will most typically range from about 0.1% to about 20%, more typically from about 0.5% to about 15%, most preferably from about 1.0% to about 10%, by weight of the scalp serum composition.

Liquid humectants suitable for use in the scalp serum compositions of the present invention include any hygroscopic, water soluble liquid having a solubility of at least 50% by weight in water at 25.degree. C. Many of these humectants will have one or more hydroxyl groups attached, non limiting examples of which include liquid polyalkylene glycols such as polypropylene glycols and diethylene or polyethylene glycols (e.g., molecular weights from about 200 to about 600, such as PEG-4, PEG-6, PEG-8. PEG-12) ethyl hexanediol, hexylene glycol, butylene glycol, glycerin, propylene glycol, dipropylene glycol, tripropylene glycol, polypropylene-5-laureth-5, polyglycerol cocoate, sorbitol, fructose, glycine, inositol, panthenol and combinations thereof.

Specific non-limiting examples of suitable humectants include Lubrajel Oil®. (glyceryl polymethacrylate and propylene glycol), Glucquat®125 (lauryl methyl gluceth-10 hydroxypropyldimonium chloride), Glucam®E-10 (methyl gluceth-10), Glucam®E-20 (methyl gluceth-20), Glucam®P-10 (PPG-10 methyl glucose ether), Glucam®P-20 (PPG-20 methyl glucose ether), sodium lactate, sodium PCA, Schercomid LME (Lactamide MEA), Clearcol (soluble collagen), Collasol M (soluble collagen), Crolastin (hydrolyzed elastin), Cromoist CS (sodium chrondroitin sulfate and hydrolyzed collagen), Cromoist HYA (hydrolyzed collagen and hyaluronic acid), Cromoist WHYA (hydrolyzed wheat protein and hylauronic acid), Cromoist O-25 (hydrolyzed oats), Cropeptide W (hydrolyzed wheat protein and hydrolyzed wheat starch), Crosilk 10,000 (hydrolyzed silk), Crosilk Liquid (silk amino acids), Crosilkquat (Cocodimonium hydroxypropyl silk amino acids), Crotein CAA/SF (collagen amino acids), Crotein HKP (hair keatin amino acids and sodium chloride, Crotein HKP/SF (keratin amino acids), Crotein MCAA (collagen amino acids), Hydrolactin 2500 (hydrolyzed milk protein), Hydrosoy 2000 (hydrolyzed soy protein), Hydrotriticum™ 2000 (hydrolyzed wheat protein), Hydrotriticum™ WAA (wheat amino acids), Reticusol (hydrolyzed reticulin), Tritisol™ (hydrolyzed wheat protein), Incromectant AMEA-100 (acetamide MEA), Incromectant AMEA-70 (acetamide MEA), Incromectant LMEA (acetmide MEA and lactamide MEA), Incromectant AQ (acetamidopropyl trimonium chloride), Incromectant LQ (lactamidopropyl trimonium chloride), Gelatin NF, Lactil® (sodium lactate and sodium PCA, and glycine and fructose and urea and niacinamide and inocitol, and sodium benzoate and lactic acid).

The humectant for use in the scalp serum composition preferably penetrates the upper layers of skin of the scalp, i.e., the stratum corneum layer, and then draws moisture into those skin layers, thus providing improved moisturization of the scalp after application. The humectant preferably helps provide the composition with the preferred skin moisturization measurements as defined hereinafter.

Product Form

The scalp serum composition of the present invention is a flowable liquid under ambient conditions and has a viscosity of from about 20 centistokes to about 60,000 centistokes, preferably from about 100 to about 20,000 centistokes. These flowable liquids can be in a variety of forms, including dispersions, multi-phase emulsions or suspensions, or single phase solutions.

It has been found that the scalp cosmetic compositions should have a product viscosity under ambient or use conditions within the ranges recited herein to provide the acceptable spreading when applied directly to the scalp, especially when applied directly to the scalp from an applicator or other packaging system designed for direct scalp application. It has also been found that scalp cosmetic compositions with zinc-containing anti-dandruff actives should have a minimum viscosity of at least 1,000 centistokes, preferably from about 1,000 to about 20,000 centistokes, to provide the desired spreading during application and to provide a uniform distribution of the active components on the applied areas of the scalp.

Hair Restoratives

The scalp serum further comprises one or more hair restorative ingredients. Preferred hair restorative actives include turmeric root extract, tocopheryl nicotinate, tocopheryl acetate, and *centella asiatica* extract.

The hair restorative extracts may be present in an amount ranging from about 0.001 wt. % to about 5 wt % of the scalp serum composition.

Method of Making

The compositions of the present invention, in general, may be made by mixing the ingredients together at either room temperature or at elevated temperature, e.g., about 72° C. Heat only needs to be used if solid ingredients are in the composition. The ingredients are mixed at the batch processing temperature. Additional ingredients, including electrolytes, polymers, fragrance, and particles, may be added to the product at room temperature.

NON-LIMITING EXAMPLES

The compositions illustrated in the following Examples illustrate specific embodiments of the compositions of the present invention, but are not intended to be limiting thereof. Other modifications can be undertaken by the skilled artisan without departing from the spirit and scope of this invention. These exemplified embodiments of the composition of the present invention provide enhanced deposition of conditioning agents to the hair and/or skin.

The compositions illustrated in the following Examples are prepared by conventional formulation and mixing methods, an example of which is described above. All exemplified amounts are listed as weight percents and exclude minor materials such as diluents, preservatives, color solutions, imagery ingredients, botanicals, and so forth, unless otherwise specified.

The following are representative of shampoo compositions of the present invention:

| Example Shampoo Composition | w.t. % |
|---|---|
| WATER\AQUA\EAU | 35.264 |
| Babassuamidiopropyl Betaine | 10.000 |
| Guar Hydroxypropyltrimonium Chloride | 0.500 |
| Sodium Hydroxide | 0.020 |
| 1,3-propanediol | 1.000 |
| Sodium Methyl Cocoyl Taurate | 15.000 |
| WATER\AQUA\EAU/SODIUM COCOYL ISETHIONATE/SODIUM LAUROAMPHOACETATE/ SODIUM METHYL COCOYL TAURATE | 2.000 |
| Disodium Laureth Sulfosuccinate | 5.000 |
| Cocamide MIPA | 5.000 |
| Sodium Cocoyl Isethionate | 4.000 |
| Stearamidopropyl Dimethylamine | 0.500 |
| Salicylic Acid | 0.150 |
| WATER\AQUA\EAU | 2.000 |
| *Vitis Vinifera* (Grape) Seed Extract | 0.100 |
| Potassium Sorbate | 0.150 |
| *CARTHAMUS TINCTORIUS* (SAFFLOWER) OLEOSOMES/GLYCERIN/WATER\AQUA\EAU | 3.000 |
| Cetrimonium Chloride | 2.000 |
| Butyl Avocadate | 0.100 |
| ETHYL MACADAMIATE | 0.250 |
| Dipotassium Glycyrrhizate | 0.025 |
| *PANAX GINSENG* (*GINSENG*) ROOT EXTRACT | 0.100 |
| Purified Water/Malt Extract/Simethicone/Acetyl Carnitine HCL/Adenosine Phosphate/Creatine/ Phenoxyethanol/Yeast Extract | 1.000 |
| Hydrolyzed Soy Protein | 0.500 |
| Citric Acid | 0.500 |
| Sodium Chloride | 1.000 |
| Fragrance (Parfum) and minors | q.s. |

| Example Conditioner Composition | w.t. % |
|---|---|
| WATER\AQUA\EAU | 81.479 |
| *PANAX GINSENG* (*GINSENG*) ROOT EXTRACT | 0.100 |
| *Vitis Vinifera* (Grape) Seed Extract | 0.100 |
| Guar Hydroxypropyltrimonium Chloride | 0.350 |
| TAPIOCA STARCH | 0.250 |
| Cetrimonium Chloride | 2.000 |
| Potassium Sorbate | 0.100 |
| Caffeine | 0.050 |
| Behentrimonium Methosulfate (and) Cetearyl Alcohol | 4.500 |
| Cetearyl Alcohol | 2.000 |
| Cetyl Alcohol | 2.000 |
| METHYL SOYATE | 1.500 |
| HYDROGENATED OLIVE OIL UNSAPONIFIABLES/ HYDROGENATED ETHYLHEXYL OLIVATE | 0.100 |
| *ALEURITES MOLUCCANA* (KUKUI) SEED OIL | 1.000 |
| *PERILLA OCYMOIDES* SEED EXTRACT/*PUNICA GRANATUM* (POMEGRANATE) SEED OIL/*SISYMBRIUM IRIO* SEED OIL ETHYL MACADAMIATE | 0.500 |
| | 0.300 |
| glyceryl caprylate | 0.300 |
| *CURCUMA LONGA* (TURMERIC) ROOT EXTRACT | 0.050 |
| *EMBLICA OFFICINALIS* FRUIT EXTRACT | 0.050 |
| Hydrolyzed Soy Protein | 0.500 |
| WATER/DIHYDROXYPROPYL ARGININE HCL | 1.000 |
| Purified Water/Malt Extract/Simethicone/Acetyl Carnitine HCL/Adenosine Phosphate/Creatine/Phenoxyethanol/Yeast Extract | 1.000 |
| Fragrance (Parfum) and minors | q.s. |

| Example Scalp Serum | w.t. % |
|---|---|
| WATER\AQUA\EAU | 26.000 |
| *Rosmarinus Officinalis* (Rosemary) Leaf Extract | 0.001 |
| Hydroxypropyl Methycellulose | 0.300 |
| Caffeine | 0.050 |
| Adenosine Phosphate | 0.040 |
| Dipotassium Glycyrrhizate | 0.100 |
| *PANAX GINSENG* (GINSENG) ROOT EXTRACT | 0.100 |
| *CAMELLIA SINENSIS* (GREEN TEA) LEAF EXTRACT | 0.050 |
| Arginine | 0.100 |
| Glucosamine HCl | 0.550 |
| PEG-40 Hydrogenated Castor Oil | 0.900 |
| *ALEURITES MOLUCCANA* (KUKUI) SEED OIL | 0.001 |
| Yeast Extract | 1.000 |
| *SACCHAROMYCES* LYSATE EXTRACT/WATER (AQUA PURIFICATA) PURIFIED/*ROSMARINUS OFFICINALIS* (ROSEMARY) LEAF EXTRACT WATER/*CHLORELLA VULGARIS* EXTRACT | 0.100 0.500 |
| Alcohol Denat. | 69.008 |
| Hydroxypropylcellulose | 0.200 |
| *Glycyrrhiza Glabra* (Licorice) Extract | 0.100 |
| Salicylic Acid | 0.050 |
| *CURCUMA LONGA* (TURMERIC) ROOT EXTRACT | 0.050 |
| Tocopheryl Nicotinate | 0.200 |
| Tocopheryl Acetate | 0.200 |
| *Centella Asiatica* (Hydrocotyl) Extract | 0.100 |
| Fragrance (Parfum) | 0.300 |

| Example Tablet | Weight in mg |
|---|---|
| Hydroxypropyl methylcellulose capsule shell | 700 |
| Aerial Parts of Gotu Kola | 50 |
| Turmeric Root | 50 |
| Green Leaf Tea | 25 |
| Triphala Powder | 50 |
| Black Pepper Extract | 5 |
| Glycerin | 520 |

All documents cited herein are, in relevant part, incorporated herein by reference; the citation of any document is not to be construed as an admission that it is prior art with respect to the present invention.

While particular embodiments of the present invention have been illustrated and described, it would be obvious to those skilled in the art that various other changes and modifications can be made without departing from the spirit and scope of the invention. It is, therefore, intended to cover in the appended claims all such changes and modifications that are within the scope of this invention.

What is claimed is:

1. A method for reducing the appearance of thinning hair in a human in need thereof comprising the successive steps of:
    a) treating the thinning human hair with an exfoliating shampoo composition comprising an effective amount of at least one chemical exfoliant;
    b) treating the thinning human hair with a conditioner comprising effective amounts of at least one natural conditioning polymer and at least one natural stimulant selected from the group consisting of ginseng and caffeine;
    c) treating the thinning human hair with a scalp serum comprising effective amounts of salicylic acid, zinc lactobionate, and at least one natural extract selected from the group consisting of ginseng root extract, *Silybum marianum* extract, *Phyllanthus emblica* fruit extract, and mixtures thereof; and
    d) ingesting by said human a capsule comprising an effective amount of one or more ingredients selected from the group consisting of gotu kola, turmeric root, green tea leaf, triphala powder, and black pepper extract.

2. A method according to claim 1, wherein said shampoo composition further comprises at least one anionic surfactant having at least one anion selected from the group consisting of sulfates, sulfonates, sulfosuccinates, isethionates, carboxylates, phosphates, and phosphonates.

3. A method according to claim 1, wherein said shampoo composition further comprises at least one cationically modified starch polymer.

4. A method according to claim 1, wherein said shampoo composition further comprises one or more surfactants selected from the group consisting of amphoteric surfactants, zwitterionic surfactants, cationic surfactants, and nonionic surfactants.

5. A method according to claim 1, wherein said shampoo composition further comprises one or more additional components selected from the group consisting of dispersed water-insoluble particles, opacifying agents, suspending agents, anti-dandruff agents, non-volatile paraffinic hydrocarbons, and propellants.

6. A method according to claim 1, wherein said at least one natural conditioning polymer is selected from the group consisting of starches, celluloses, and/or guars.

7. A method according to claim 1, wherein said chemical exfoliant is selected from the group consisting of salicylic acid, glycolic acid, enzymes, citric acid, malic acid, alpha hydroxyl acid, beta hydroxyl acid, and mixtures thereof.

* * * * *